(12) United States Patent
Ehmke et al.

(10) Patent No.: US 10,512,567 B2
(45) Date of Patent: Dec. 24, 2019

(54) SOFT ABSORBENT SANDWICH WEB COMPRISING HIGH CONCENTRATIONS OF SUPERABSORBENT MATERIAL, CELLULOSIC FIBERS AND SURFACE APPLIED BINDER

(71) Applicant: GLATFELTER FALKENHAGEN GMBH, Pritzwalk (DE)

(72) Inventors: Ralf Ehmke, Meyenburg (DE); Henning Röttger, Kaltenkirchen (DE); Reno Volkmer, Pritzwalk (DE)

(73) Assignee: GLATFELTER FALKENHAGEN GMBH, Pritzwalk (DE)

( * ) Notice: Subject to any disclaimer, the term of this patent is extended or adjusted under 35 U.S.C. 154(b) by 898 days.

(21) Appl. No.: 14/414,414

(22) PCT Filed: Jul. 12, 2013

(86) PCT No.: PCT/EP2013/064749
§ 371 (c)(1),
(2) Date: Jan. 12, 2015

(87) PCT Pub. No.: WO2014/009506
PCT Pub. Date: Jan. 16, 2014

(65) Prior Publication Data
US 2015/0164710 A1   Jun. 18, 2015

(30) Foreign Application Priority Data
Jul. 13, 2012   (GB) .................... 1212459.0

(51) Int. Cl.
*A61F 13/537*     (2006.01)
*A61F 13/53*      (2006.01)
*A61F 13/534*     (2006.01)
*B32B 5/26*       (2006.01)
*B32B 37/10*      (2006.01)

(52) U.S. Cl.
CPC .............. *A61F 13/537* (2013.01); *B32B 5/26* (2013.01); *B32B 37/1018* (2013.01); *A61F 2013/53445* (2013.01); *A61F 2013/530481* (2013.01); *B32B 2250/03* (2013.01); *B32B 2250/40* (2013.01); *B32B 2255/02* (2013.01); *B32B 2255/26* (2013.01); *B32B 2262/04* (2013.01);
(Continued)

(58) Field of Classification Search
CPC .......................................... A61F 2013/530481
See application file for complete search history.

(56) References Cited

U.S. PATENT DOCUMENTS 3,575,174 A    4/1971  Mogor
4,781,710 A   11/1988  Megison et al.
(Continued)

FOREIGN PATENT DOCUMENTS

CA    2 787 887 A1    8/2011
CN     1303255  A     7/2001
(Continued)

*Primary Examiner* — Peter S Vasat
(74) *Attorney, Agent, or Firm* — Blank Rome LLP

(57) ABSTRACT

The present invention is a liquid absorbent sandwich web as can be used in absorbent products such as in disposable absorbent articles such as diapers, feminine hygiene articles or incontinence devices, and to the manufacturing of such webs. The liquid absorbent sandwich web provides high absorbent capacity without compromising softness.

20 Claims, 1 Drawing Sheet

(52) U.S. Cl.
CPC ....... *B32B 2317/18* (2013.01); *B32B 2555/02* (2013.01); *Y10T 442/659* (2015.04)

(56) References Cited

U.S. PATENT DOCUMENTS

| | | |
|---|---|---|
| 4,898,642 A | 2/1990 | Moore et al. |
| 5,244,482 A | 9/1993 | Hassenboehler, Jr. et al. |
| 5,378,528 A * | 1/1995 | Makoui ............ A61F 13/15642 428/219 |
| H1565 H | 7/1996 | Brodof et al. |
| 5,549,589 A | 8/1996 | Horney et al. |
| 5,607,414 A | 3/1997 | Richards et al. |
| 2003/0024092 A1* | 2/2003 | Orlandi .................... B32B 5/26 28/104 |
| 2004/0122394 A1 | 6/2004 | Fell et al. |
| 2004/0167487 A1* | 8/2004 | Tamburro ............... A61L 15/28 604/367 |
| 2004/0214499 A1 | 10/2004 | Qin et al. |
| 2008/0234645 A1* | 9/2008 | Dodge .................... A61L 15/18 604/368 |
| 2011/0184365 A1 | 7/2011 | Röttger et al. |
| 2013/0288556 A1* | 10/2013 | Moore ................... D04H 1/435 442/334 |

FOREIGN PATENT DOCUMENTS

| | | |
|---|---|---|
| CN | 1507336 A | 6/2004 |
| CN | 1157169 C | 7/2004 |
| CN | 1164250 C | 9/2004 |
| CN | 1833623 A | 9/2006 |
| CN | 100486802 C | 5/2009 |
| EP | 0 272 682 A2 | 6/1988 |
| EP | 0 443 627 A2 | 8/1991 |
| EP | 0 725 418 B1 | 3/1999 |
| EP | 0 725 613 B1 | 3/1999 |
| EP | 0 725 615 B1 | 3/1999 |
| EP | 0 725 616 B1 | 3/1999 |
| EP | 0 725 892 B1 | 7/2001 |
| EP | 1 032 342 B1 | 7/2001 |
| EP | 0 397 110 B2 | 3/2002 |
| EP | 1 353 001 A1 | 10/2003 |
| EP | 1 721 036 B1 | 2/2008 |
| EP | 1 621 165 B1 | 4/2010 |
| EP | 1 621 166 B1 | 9/2010 |
| GB | 2 284 549 A | 6/1995 |
| JP | 2001-96654 A | 4/2001 |
| JP | 2005-520722 A | 7/2005 |
| WO | WO 95/26209 | 5/1995 |
| WO | WO 97/38654 | 10/1997 |
| WO | WO 99/49826 A1 | 10/1999 |
| WO | WO 00/71790 A1 | 11/2000 |
| WO | WO 01/87215 A1 | 11/2001 |
| WO | WO 2011/092025 A1 | 8/2011 |
| WO | WO 2012/048878 A1 | 4/2012 |

\* cited by examiner

SOFT ABSORBENT SANDWICH WEB COMPRISING HIGH CONCENTRATIONS OF SUPERABSORBENT MATERIAL, CELLULOSIC FIBERS AND SURFACE APPLIED BINDER

FIELD OF THE INVENTION

The present invention relates to absorbent webs as can be used in absorbent products such as in disposable absorbent articles such as diapers, feminine hygiene articles or incontinence devices, in food pads, bed pads, pet pads and the like, and to the manufacturing of such webs. The present invention can particularly well be applied to air-laid webs.

BACKGROUND

Composite structures comprising superabsorbent material are well known, in particular for applications in absorbent articles, such as disposable absorbent articles, such as baby or adult incontinence diapers, feminine hygiene products, food pads, bed pads, pet pads and the like. In addition to effectively and efficiently satisfy the primary liquid handling functionality of acquisition, distribution and storage of the exudates, the perception and acceptance by the user, in particular for a wearer, such as with regard to wearing comfort or discreteness has become more and more an area of attention.

In particular for absorbent disposable articles, there has been recently a trend towards thinner articles. In this context, superabsorbent materials (SAM) have been used in increasing concentrations, initially without majorly changing the design principles of the articles or of the production facilities.

In this context, first limitations by superabsorbent properties have been addressed such as described in WO95/26209 (P&G, Goldman) and products with a maximum concentration of up to about 60 weight-% of SAM particles became broadly distributed, if not a standard in baby diapers. Such structures allowed production on existing diaper manufacturing equipment, where the SAM and the cellulosic fibers were mixed in-line, i.e. the SAM particles were provided in bulk form to the manufacturing plant and mixed with defiberized cellulose. Then an absorbent core was formed and directly combined with chassis elements like topsheet and backsheet for making a finished diaper.

Taking the minimization of cellulosic fibers to the extreme resulted in the "air felt free" technology, where at least the liquid storage component of an absorbent article is essentially free of cellulosic fibers. This has been described e.g. in EP725613A1, EP725615A1, EP725616A1, EP724418A1 (all K-C, Tanzer); EP1621165A1, EP1621166A1 (P&G, Blessing); WO2012/048878A1 (Romanova BvBA Starter, van de Maele), all disclosing pocketed structures with superabsorbent particles sandwiched between webs. In order to satisfy manufacturing and in-use requirements the SAM particles are immobilized by positioning these in "pocket structures", optionally by the application of adhesive.

However, such structures have some drawbacks. So they require particular and sometimes complicated process measures to satisfy modern high speed production requirements. Further, they require particular measures with regard to fluid handling as such high concentration superabsorbent structures are limited in their ability to distribute liquid. Also measures need to be taken to immobilize the superabsorbent particles both in their dry and in their wet state. Even further, such structures may exhibit a hard feel to the user, as the particulate material may give a hand, which may be referred to as "sanding paper" like.

Yet a further approach of improving absorbency has been followed in the field of air-laid materials. Such materials are also well known in the art and are broadly commercially distributed. They also comprise cellulosic fibers, and often SAM. However, such materials are typically produced "off-line" and shipped as a composite to a converter, who may form absorbent articles, but also other absorbent products such as food tray pads.

Airlaid materials may—and often do—comprise binder materials so as to enhance the mechanical stability and SAM immobilization at least in the dry state, often also in the wet state. Typically airlaid materials exhibit very good softness and feel to the touch.

In EP1032342A1 (Maksimow) structures are described, which may comprise up to 70% of particulate SAM, the remainder being cellulosic fibers. The binding of the structure is described to be essentially only achieved by "fusion bonding" between cellulosic fibers, induced by the residual moisture of the fibers and a high compaction pressure.

In WO99/49826 a C-folded layered absorbent core is described, wherein an absorbent layer is positioned between an upper and a lower layer. These latter layers may comprise latex as a bonding agent. Whilst the absorbent layer may exhibit SAM concentrations of up to 95% by weight, the total absorbent core exhibits SAM concentrations of below 70% by weight.

In EP1721036A1 (Glatfelter, Hansen) the manufacturing of fibrous webs with low dustiness and good liquid handling and mechanical strength is described. To this end, a mixture of SAM particles and cellulosic fibers can be sprayed on both sides with a high moisture content latex dispersion. Upon embossing and drying, optionally combined with vacuum suction for a controlled penetration of the latex dispersion or at least the water phase thereof, three bonding mechanism are described to take place: First, the "self bonding" of pressure bonding due to the natural moisture of the fibers. Second, the outer regions of the web as exposed to the latex resin are bonded upon curing of the latex. Thirdly, the penetration of the moisture into the web further creates hydrogen bonding.

As the bonding mechanism relies on fiber-to-fiber bonds, this approach is—similar to the technology as described in EP'342 (Maksimov)—limited to a maximum SAM particle concentration of about 70%

In spite of all these approaches, there is still a need for providing an absorbent structure which provides high absorbency by exhibiting high concentrations of SAM in excess of 70%, which exhibits good liquid handling properties but also good tactile properties.

There is also a need for providing such materials for being included in disposable absorbent products.

Even further, there is a need for an easy and effective manufacturing process for such structures, which may be also be executed for the manufacturing of off-line air-laid structures.

SUMMARY

In a first aspect, the present invention is a liquid absorbent sandwich web, exhibiting in Cartesian coordinates an essentially endless (x-directional) length along the machine direction of the manufacturing process, further a thickness or z-direction and a width (y-) direction. The absorbent web comprises as sandwich forming materials a first and a second outer layer, in the form of an in-situ formed or pre-formed web, preferably comprising cellulosic fibers;

superabsorbent material (SAM) sandwiched between the outer layers, preferably particulate SAM;

individualized fibers adapted to be interspersed between the SAM, preferably comprising cellulosic fibers;

a self-crosslinking latex binder.

The self-crosslinking latex may be present in at least one of the first and the second outer layer and in the mixture of the SAM and the fibers between the first and the second layers.

The sandwich forming materials are present in the absorbent web in the following composition, which is essentially uniform across the x- and y-direction of the web:

SAM from about 70% to about 90%;

fibers interspersed between the SAM from about 5% to 25%;

first outer layer from about 2% to about 15%;

second outer layer from about 2% to about 15%;

self-crosslinking latex binder from about 1% to about 5% all as weight-% based on the sum of the weights of the sandwich forming materials.

In a preferred execution, the liquid absorbent web exhibits at least one of the following of SAM from about 80% to about 90%;

fibers interspersed between the SAM from about 8% to 15%;

first outer layer from about 2% to about 10%;

second outer layer from about 2% to about 10%;

self-crosslinking latex binder from about 2% to about 4%.

Preferably, the self-crosslinking latex binder is a vinlyacetate-ethylene copolymer. Preferably, the web comprises less than about 5%, preferably less than about 1%, more preferably less than about 0.1% other binder material, based on the amount of SAM, fibers, and binder.

Preferably, the absorbent sandwich web exhibits at least one of the following:

an absorbent web centrifuge retention capacity which is at least 23 g/g, preferably more than 24 g/g, more preferably more than 25 g/g according to a method as described herein;

an absorbent web centrifuge retention capacity which is at least 85%, preferably more than 90%, more preferably more than 93% of the SAM centrifuge retention capacity;

a stiffness to capacity ratio as determined by the ratio of the web material stiffness and the area specific capacity, as described herein, of less than 5.0, preferably less than 3.0, more preferably less than 2.5, and most preferably less than 2.0, all in units of $(mNcm)/(1/m^2)$.

A disposable absorbent article may comprise such an absorbent web sandwiched between a topsheet, a backsheet. An intermediate layer may be positioned between the absorbent web and the topsheet.

In a further aspect, the present invention is a method for the making of a liquid absorbent web exhibiting in Cartesian coordinates an essentially endless (x-directional) length along the machine direction of the manufacturing process, further a thickness or z-direction and a width (y-) direction.

The method comprises the following steps of providing a first and a second outer layer, in the form of an in-situ formed or pre-formed web,
preferably comprising cellulosic fibers;
superabsorbent material (SAM),
preferably particulate SAM;
individualized fibers,
preferably cellulosic fibers;
a self-crosslinking latex binder;

forming a mixture of SAM and essentially individualized fibers,
at a SAM concentration of at least 70% based on the combined weight of SAM and fibers in the mixture;

forming a sandwich structure of the mixture between the first and the second outer layer at an essentially constant thickness, basis weight and concentration along the (x-)-length and (y-) width direction of the web;

applying a self-crosslinking latex binder to at least one of the outer surfaces of the outer layers;
preferably at an amount of at least 1%, more preferably more than 2% and preferably at an amount of not more than 5%, more preferably not more than 4%, based on the dry amount of latex binder in the absorbent web;

thermally treating the sandwich structure for reducing moisture content and inducing crosslinking of the self-crosslinking latex binder;

compacting the sandwich structure in one or more compaction step(s);

optionally applying vacuum suction z-directionally through the sandwich structure.

Preferably, the maximum line pressure of any of the one or more compaction steps is less than about 60 N/mm, preferably less than about 30 N/mm. Preferably, at least one of the compaction steps is executed at a line pressure of more than about 10 N/mm, preferably more than 15 N/mm. The self-crosslinking latex binder may be applied as an aqueous solution or dispersion, preferably at a self-crosslinking latex binder content of more than 5%, preferably more than about 10%, preferably less than about 30%, preferably less than about 25%, more preferable less than about 20%, all based on dry matter of the latex binder in the solution or dispersion.

Preferably the thermal treatment of the sandwich structure is at between 130° C. and 180° C., preferably between 130° C. and 150° C. Preferably, the thermal treatment is executed until a final overall moisture content of the absorbent web is less than 15%, preferably less than 10%, more preferable less than 6%.

DETAILED DESCRIPTION

Figure 1:
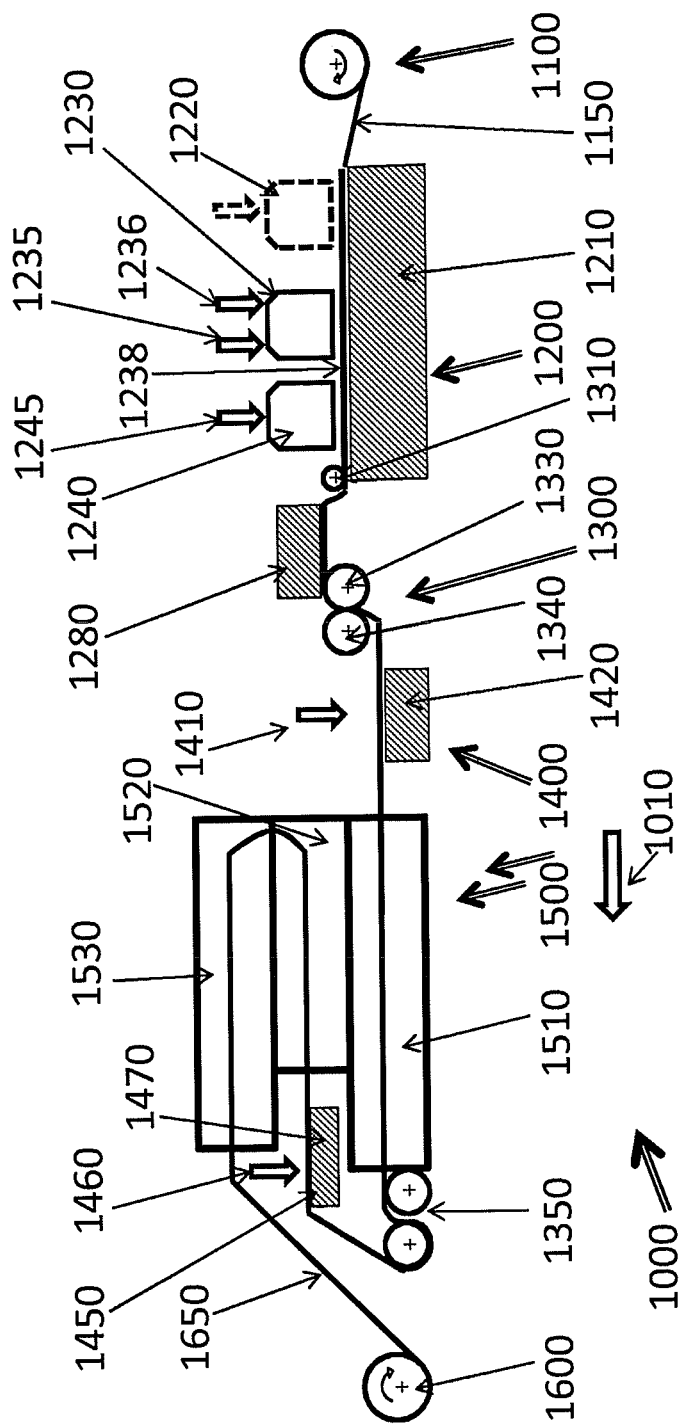
FIG. 1 shows schematically an exemplary process set up for manufacturing a liquid absorbent sandwich web according to the present invention.

Reference will now be made in detail to embodiments of the invention, which are intended to illustrate the present invention by way of explanation but which not necessarily are meant as a limitation of the invention. For example, features illustrated or described as part of one embodiment can be used with another embodiment to yield still a third embodiment. It is intended that the present invention include these and other modifications and variations.

Unless otherwise specified, all percentages are expressed as "weight-%".

In a first aspect, the present invention is a liquid absorbent sandwich web.

The term "web" or "web material" refers to an essentially endless material in one direction, i.e. the longitudinal extension, or the length, or the x-direction in Cartesian coordinates relative to the web material. Included in this term is an essentially unlimited sequence of pieces cut or otherwise separated from an essentially endless material. Typically the web materials will have a thickness dimension (i.e. the z-direction) which is significantly smaller than the longitudinal extension (i.e. in x-direction). Typically, the width of web materials (the y-direction) will be significantly larger than the thickness, but less than the length. Often, though not necessarily, the thickness and the width of such materials is essentially constant along the length of the web. Without intending any limitation, such web materials may be cellulosic fiber materials, tissues, woven or non-woven materials and the like. Typically, though not necessarily, web materials are supplied in roll form, or on spools, or in a folded state in boxes. The individual deliveries may then be spliced together to form the essentially endless web. A web material may be composed of several web materials, such as multilayer non-woven, coated tissues, non-woven/film laminates. Web materials may comprise other materials, such as added binding material, particles, in particular superabsorbent particles, hydrophilizing agents and the like.

If a web comprises fibers, these are typically bonded to each other or to other components of a web, such as other webs, such as films or fibrous webs exhibiting sufficient strength. There are many suitable bonding mechanisms available, such as thermal or melt fusion bonding, including ultrasonic bonding, or adhesive application.

Webs may be pre-fabricated separately, and may be stored and/or transported before being processed further. Alternatively, webs may be formed in-situ, i.e. during the converting process of making products or semi-finished products by combining such webs with other webs and/or other materials. A web may comprise several layers, each or which may be pre-fabricated or in-situ formed, or which may comprise a pre-fabricated web to which other materials, optionally forming a web, are added.

If a web is pre-manufactured, it needs to sustain normal processing stresses, such as occur during handling, storage or transport and transfer, and thus pre-manufactured webs are typically pre-bonded.

Within the present context, the term "absorbent" and related terms refer to the ability of a material to receive liquids and to retain such liquids under certain conditions. Thus a material such as a cellulosic web can absorb aqueous liquids essentially by two mechanisms, namely retaining some water within the fibrous structure and by retaining liquids and possibly other materials dispersed in the liquid in interstitial voids between fibers. Accordingly, the term "superabsorbent material" or "SAM", also referred to as "superabsorbent", "absorbent gelling material" or "AGM", "absorbent polymer material" means partially cross-linked polymeric materials, which can absorb water whilst they are swelling to form a gel. Typically, they can absorb at least 10 times their own weight, often more than 20 times or even more than 30 times their own weight when determined according to the centrifuge retention capacity as described in more detail herein below.

Liquids as may be suitably absorbed by the present invention are generally aqueous liquids, such as bodily exudates such as urine, menses, low viscosity faeces, blood, etc. Such liquids may be emanating from bodily openings of living humans respectively animals, but may also leak or spill from wounds or from foods like meat or fruits.

The liquid absorbent web according to the present invention is in the form of a x-y-directionally homogeneous sandwich, i.e. the composition is not intentionally varying, apart from normal process fluctuations or edge effects.

Within the present context, the term sandwich refers to a web structure with at least three layers, plies, or strata, which are positioned z-directionally adjacently in a facing relationship such that the first and the opposite second surface of the central layer contacts the inwardly facing surfaces of the respective outer layers.

The present invention applies particularly to sandwich webs which are essentially homogeneous in their x-y-direction.

Within the present context, the central layer comprises SAM, preferably SAM particles, and essentially individualized fibers, preferably cellulosic fibers, and is formed in-situ during the manufacturing according to the present invention, as will be discussed in more detail herein below.

Whilst superabsorbent materials may have various shapes and forms, such as irregular or spherical particles, flakes, fibers or spongelike structures, they are most often used as irregularly shaped granules, having a mean particle size of from 10 μm to 1000 μm, preferably with less than 5% having a particle size of 5 μm, and preferably with less than 5% having a particle size of more than 1200 μm.

It has been found beneficial to use a particulate SAM for absorbent webs according to the present invention. Preferably, the SAM exhibits good absorbent properties of more than about 20 g/g, preferably more than about 25 g/g, more preferably more than 30 g/g, as determined by the centrifuge retention capacity method according to the well known method EDANA 441.2-02 resp. WSP241.2 (SAM-CRC). Without wishing to be bound by theory it is believed that such material, even in the swollen state, i.e. when liquid has been absorbed, does not substantially obstruct the liquid flow throughout the material, especially when the permeability as expressed by the saline flow conductivity of the absorbent polymer material is greater than 10, 20, 30 or 40 SFC-units, where 1 SFC unit is $1\times10^{-7}$ $(cm^3\times s)/g$. Saline flow conductivity is a parameter well recognized in the art and is to be measured in accordance with the test disclosed in EP0752892 B (Goldman et al; P&G). Such materials are commercially available such as from Evonik Stockhausen GmbH, Germany, BASF SE, Germany, or Nippon Shokubai KK, Japan. A particular suitable material is EK-X EN52 of Ekotec Industrietechnik GmbH, Germany.

The central layer further comprises fibrous material. Generally, the selection of useful fibers is not critical, as long as the fibers do not negatively impact the packing of the SAM. Conventional synthetic fibers as well known in the art can be employed as well as various natural material based fibers such as made from viscose/rayon. Also mixtures or blends of different fiber types can be employed. Preferably the fibers are not restricting the swelling of SAM, and as such do not exhibit adhesive properties, in particular in a wet state.

Whilst it may not be preferred from an operational and/or cost point of view, special fiber treatment, such as fibrillation or the use of high surface area or nano-fibers can be employed.

Such high surface area fibers include glass microfibers such as, for example, glass wool available from Evanite Fiber Corp. (Corvallis, Oreg.), which typically have fiber diameters of not more than about 0.8 μm, more typically from about 0.1 μm to about 0.7 μm. These microfibers will have surface areas of at least about 2 $m^2/g$, preferably at least about 3 $m^2/g$. Typically, the surface area of glass microfibers; will be from about 2 $m^2/g$ to about 15 $m^2/g$. Representative glass microfibers for use herein are those available from Evanite Fiber Corp. as type 104 glass fibers, which have a nominal fiber diameter of about 0.5 μm. These glass microfibers have a calculated surface area of about 3.1 $m^2/g$.

Another type of high surface area fibers are fibrillated cellulose acetate fibers. These fibers (also referred to as "fibrets") have high surface areas relative to cellulose-derived fibers commonly employed in the absorbent article art. Such fibrets have regions of very small diameters, such that their particle size is typically from about 0.5 to about 5 μm. These fibrets typically have a surface area of about 20 $m^2/g$.

In a particular execution, the fibrous material comprises or predominantly (i.e. at more than 50%) or even essentially consists of conventional cellulose as broadly used in the hygiene industry. Preferably it is made by the Kraft-process, more preferably without the use of elemental chlorine. Preferred wood species are southern pine or northern softwood. Typically, the length weighted average fiber length is more than about 2 mm but less than about 3.5 mm, and the weight weighted average length is between 3 and 4 mm. Typically the moisture content, also referred to as residual or natural moisture content of such a wood pulp material is between 6% and 10%. The cellulosic fibers may be treated with debonding agents, such as well known in the art. Typically the cellulose is supplied in the form of densified rolls, which are disintegrated into individualized fibers by hammer mills or equivalent techniques.

A particularly suitable material is Golden Isles EG-100 Airlaid fluff pulp Grade 4881, available from Georgia-Pacific, USA, at a standardized residual moisture content of 8%. The SAM and the individualized fibers are mixed together to form the central layer. This mixing can be achieved by any conventional means which ensures good distribution of the SAM and the fibers, such as by the well known technology of M&J Fibertech A/S, Denmark.

The central layer according to the present invention comprises high amounts of SAM, at least more than about 75%, more preferably more than 80% or even more preferably 90%, all these percentages based on the combined weight of SAM and fibers in the central layer.

As the central layer according to the present invention comprises relatively high amounts of SAM, it is believed that the fibers do not form a fibrous structure with SAM particles interspersed, but that the SAM particles form a particle matrix with fibers interspersed in the interparticle interstices.

It is preferred that the SAM can swell as unrestricted as possible. To this end, it is further preferred, that the central layer does not comprise materials restricting the swelling, in particular no binder materials, at least no moisture resistant binder. If such binder material is present this should be at no more than about 5% parts, preferably less than about 1%, and more preferably less than about 0.1% based on the combined weight of SAM, fibers and binder in the central layer.

The outer layers may be pre-fabricated and/or pre-bonded webs, or may be formed in-situ, optionally bonded prior to be combined with the other web(s) to form a sandwich. In addition to serve as a processing aid, the main functionality of the outer layers is to enhance the integrity and the mechanical properties of the sandwich web. Of course, the webs can also contribute to the liquid handling properties of the web, such as providing absorbent capacity, or enhancing liquid distribution properties.

In a first execution the outer layers can be pre-fabricated and can be supplied to the making of the sandwich web as bonded webs. Such webs may be comprise or even essentially consist of synthetic fibers, such as well known non-woven materials. Without intending any restriction, particular non-woven materials are made from polypropylene by spun-melt processes, which may comprise spunbonding (S) and/or melt-blowing (M) sub-strata in various combinations, such as spunbonded webs, SMS, SSMMSS etc., such as well known to a person skilled in the art. Suitable webs may also comprise staple fibers and may have been formed by carding or other methods, all well known in the art. Such webs may be suitably hydrophilized, optionally permanently. Suitable webs may exhibit basis weights of less than about 30 $g/m^2$, often less than 20 $g/m^2$.

Other webs may comprise or essentially consist of cellulosic fibers, such as well known paper tissues. A particular suitable tissue is a 17 $g/m^2$ paper tissue available under the trade designation KB 1730-001 from Swedish Tissue AB, Sweden.

In a further execution, the outer layers may be formed in-situ. This refers to the situation, that fibers are individualized or even produced on the same machine as producing the sandwich web. The in-situ formed web may be formed as a first layer onto which the SAM/fiber mixture is laid down. Alternatively or additionally the in-situ formed web may be formed after the SAM/fiber mixture is laid down.

Depending on the selection of the outer layers the separation between them and the central layer may be more or less sharply pronounced. If, for example, the SAM/fiber mixture is laid down onto a pre-formed first tissue (then called the "carrier" web) and second tissue (then called the "cover" web) is placed over the mixture, the separation between the layers can be very distinct.

If the SAM/fiber mixture is laid down onto an open pore non-woven web, some of the fibers or even particles may penetrate into the web and the separation may be less sharp. If the SAM/fiber mixture is laid onto an in-situ formed layer of fibers of the same type, or if such fibers are in-situ laid over the mixture, the distinction may become less sharp. However, in all cases there is a discontinuity in the properties of the web along the z-directional axis, as may be determined by appropriate tools, such as microphotography, x-ray analyses etc.

The absorbent sandwich web according to the present invention further comprises a latex binder as well known in the industry. Within the present context, the term latex binder refers to polymeric materials that are applied to a substrate in an uncured state, typically as an aqueous dispersion. Upon thermally treating the substrate both drying of the water as carrier and thermally induced curing of the latex binder occurs.

In view of avoiding undesired components such as formaldehyde as may be released by certain binder formulations, preferred synthetic polymers that can be used in binder latexes include polymers or copolymers of alkylacrylates, vinyl acetates such as ethylene vinyl acetate, and acrylics such as styrene-butadiene acrylic. Latexes useful in the present invention may be prepared by emulsion polymerization of certain olefinic (ethylenically unsaturated) monomers. This emulsion polymerization can be carried out by customary methods using any of a variety anionic, nonionic, cationic, zwitterionic and/or amphoteric emulsifiers to stabilize the resultant latex, including alkyl sulfates, alkylaryalkoxy sulfates, alkylarylsulfonates and alkali metal and/or ammonium salts of alkyl- and alkylaryl-polyglycol ethersulfates; oxyethylated fatty alcohols or oxyethylated alkylphenols, as well as block copolymers of ethylene oxide and propylene oxide; cationic adducts of primary, secondary or tertiary fatty amines or fatty amine oxyethylates with organic or inorganic acids, and quaternary alkylammonium surfactants; and alkylamidopropylbetaines. The olefinic monomer can be a single type of monomer or can be a mixture of different olefinic monomers, i.e. to form copolymer particles dispersed or emulsified in the aqueous phase. Examples of olefinic monomers that can be used to form latex polymers include $C_2$-$C_4$ alkyl and hydroxy alkyl acrylates, such as those selected from the group of propyl acrylate, n-butyl acrylate, isobutyl acrylate, 2-hydroxyethyl acrylate, 2-hydroxypropyl acrylate, ethyl acrylate and mixtures thereof. Other examples are $C_1$-$C_4$ alkyl or hydroxy alkyl methacrylates selected from the group of propyl methacrylate, n-butyl methacrylate, isobutyl methacrylate, 2-hydroxyethyl methacrylate, 2-hydroxypropyl methacrylate, ethyl methacrylate, methyl methacrylate, vinyl acetate and mixtures thereof. Also suitable are mixtures of the aforementioned $C_2$-$C_4$ alkyl and hydroxy alkyl acrylates and $C_1$-$C_4$ alkyl or hydroxy alkyl methacrylates. A particularly preferred execution of such a binder latex are a self-crosslinking aqueous polymeric dispersion of a vinylacetate-ethylene copolymer.

Suitable binder latexes may exhibit a glass-transition temperature of more than about 0° C. but less than about 30° C., preferably of between 5° C. and 15° C. The polymer dispersion may have a particle size of from 0.01 to about 10 μm, preferably between about 0.1 and 3 μm.

A specific execution of such a material is Vinnapas® 192, commercially available from Wacker Chemie AG, Germany.

The latex binder is at least applied to the sandwich structure to an outer surface of the outer layers as an aqueous uncured dispersion. Due to the absorptive properties of the outer layers the aqueous dispersion will penetrate into the outer layers, whereby the dispersed polymer may be retained by the filtering effect of the outer layers more towards the surface, whilst the water may penetrate z-directionally deeper into the sandwich structure.

At application of a thermal treatment at least a portion, preferably all, of the carrier water is dried off and the polymer is cured.

Thus, a liquid absorbent sandwich web according to the present invention comprises the following elements at percentages based on the total weight of the absorbent sandwich web:
  A center layer comprises at least 70%, preferably 75%, more preferably more than 80%, and most preferably more than 85% SAM mixed with between 5% and 25% fibers, preferably cellulosic fibers interspersed therein. Preferably the centre layer comprises at most 5%, more preferably less the 1%, and most preferably less than 0.1% of added binder material, based on the amount of SAM, fibers and binder material in the central layer.
  Two outer layers positioned on the respective opposite surfaces of the center layer, each at an amount of between 2% and 15% of the total sandwich web.
  Latex binder applied to the surfaces of the outer layers at an amount of between 1% and 5%.

In a preferred execution, each of the percentages of the composition may be narrowed to the following ranges:
  SAM from about 80% to about 90%;
  fibers interspersed between the SAM from about 8% to 15%;
  first outer layer from about 2% to about 10%;
  second outer layer from about 2% to about 10%;
  self-crosslinking latex binder from about 2% to about 4%.

A liquid absorbent sandwich web according to the present invention exhibits particular properties.

An important property of absorbent webs is the absorbent capacity, as may be suitably determined by as web centrifuge retention capacity (w-CRC), such as determined by applying the EDANA method 441.2-02 resp. WSP241.2 (2005), modified in that a 10 minutes drip time is introduced after the 30 minutes immersion time and by extending the centrifugation time to 5 minutes. Preferably an absorbent sandwich web according to the present invention exhibits a w-CRC value of at least 23 g/g, more preferably or more than 24 g/g and even more preferably more than about 25 g/g.

Preferably, the sandwiching does not restrict the swelling of the SAM. This can be determined when comparing the SAM-CRC value of the pure SAM with the w-CRC of the absorbent sandwich web. Thus, preferably a sandwich web exhibits a w-CRC which is at least 80%, preferably more than 90% of the SAM-CRC value of the pure SAM multiplied by the percentage of SAM in the sandwich web.

In particular with regard to modern designs of absorbent articles, the thickness of an absorbent web relative to its capacity is an important property, as can be expressed by the area specific capacity ($1/m^2$), as can be determined by measuring the w-CRC value and multiplying it with the basis weight of the sandwich web, which can be determined according to EDANA method 40.3 resp. WSP 130.1. Accordingly, the area specific capacity of sandwich web according to the present invention can be up to 10 $1/m^2$ or even more, such as 12 $1/m^2$ or more.

Another important property for a sandwich web is the strength of the total web so as to withstand mechanical stress during processing and in use. Preferably, a sandwich web according to the present invention exhibits a tensile strength of at least 10 N/50 mm, preferably more than 20 N/50 mm, or even well above 40 N/50 mm, as may be determined by the EDANA method 20.2 resp. WSP. 110.4.

However, the high SAM percentage and the mechanical strength should not negatively impact the haptic properties of the material. Whilst this is a multifaceted area, a first approach for assessing softness of a sandwich web is to determine the bending stiffness according to EDANA method 50.5 resp. WSP 90.5 and to relate the result to the area specific capacity (see above). Preferably, an absorbent sandwich web according to the present invention exhibits stiffness-retention-ratio of less than 5.0, preferably less than 3.0, more preferably less than 2.5, and most preferably less than 2.0, all in units of (mNcm)/($1/m^2$).

Yet a further approach towards determining the haptic properties is the use of the so called "Handle-O-Meter" test, according to the EDANA method WSP 90.3.0, modified by evaluating samples of 40 mm×160 mm and by setting the slot width to 20 mm. Suitable sandwich webs exhibit results of less than 5 N/200 mm, preferably of less than about 3 N/200 mm.

Yet a further property of the sandwich web relates to the immobilization of the SAM, especially when in particulate form. Preferably, the SAM remains immobilized during processing, transport and use, i.e. both under dry and wet conditions. A web according to the present invention achieves good immobilization by various effects:

First, the latex binder as applied to the outer layers provides at least bonding of the outer layers: However, at least some of the latex binder will penetrate deeper towards the central layer. The penetration depth can be adjusted by various ways, including the concentration of the latex binder in the application dispersion relative to the thickness and basis weight of the outer layers.

Further, upon application even of moderate compaction pressure, as will be discussed in more detail herein below, even the low level of residual moisture in cellulosic fibers can result in attachment of the fibers to SAM. Without wishing to be bound by a theory, it is believed that hydrogen bonding provides bonding at least in the dry state. It should be noted, that this bonding is a different mechanism as compared to conventional fiber dominated structures, where hydrogen bonding occurs between fibers rather than between fibers and SAM.

As a third mechanism it is believed that the amount of water from the phase of the latex binder dispersion can be adjusted such that a predetermined amount of water penetrates into the central layer, where it can promote further hydrogen bonding.

As the bonding in the central layer is believed to be primarily based on hydrogen bonding, this provides for good immobilization under dry conditions. However upon wetting, this bonding is loosened and the SAM can swell freely. The overall web integrity is provided by the outer layers, enhanced by the latex binder.

The dry integrity of a sandwich web can be assessed by the Composite Lamination Strength test, EDANA WSP 401.0 (05). When applying the test, the outer layer preferably delaminates from the center layer, thereby exhibiting a lamination strength of at least 0.5 N/50 mm, preferably more than about 1.0 N/50 mm, more preferably more than 1.5 N/50 mm.

An absorbent sandwich web according to the present invention is particularly useful as a liquid absorbent core in disposable absorbent articles.

Such articles are well known in the art, and comprise a liquid permeable material positioned towards the wearer during use, a liquid impermeable material opposite thereof oriented away from the user during use. The liquid absorbent core is positioned between these layers, and may comprise a sandwich web according to the present invention. Preferably the article comprises materials adapted to enhance the liquid handling properties of the article positioned between the liquid absorbent core and the topsheet. As the sandwich webs according to the present invention are primarily designed to provide liquid storage capability, additional material may enhance the liquid distribution and optionally intermediate storage capability.

Such materials are well known to a person skilled in the art of designing absorbent articles, and have been described e.g. in EP0397110A1 (Latimer) disclosing a surge management portion for improved fluid handling, having specific basis weights, acquisition times and residual wetness;

U.S. Pat. No. 4,898,642 (Moore et al.) discloses specially twisted, chemically stiffened cellulosic fibers and absorbent structures made there from;

U.S. Pat. No. 3,575,174 or 4,781,710 disclose that parts of the liquid distribution structure are compressed to a higher density, thus creating smaller pores for increased;

U.S. Pat. No. 5,244,482 (Hassenboehler) aiming at reducing maximum pore size by stretching a fibrous structure comprising meltable fibers in one direction and "freezing" the deformation by heat curing.

Also, special material composites were developed, aiming at allowing to tailor the pore size and pore size distribution. Examples for such improvements are described in greater detail in U.S. Pat. No. 5,549,589 (Homey et al.) or in PCT application WO 97/38654 (Seger et al.). Both aim essentially at providing a resilient structure by using specially stiffened cellulosic fibers such as crosslinked cellulose softwood fibers, and by filling the large pores with small and thin cellulosic fibers such as eucalyptus fibers. Both applications further add means for providing sufficient integrity and strength to the structure, the first one (U.S. Pat. No. 5,549,589) by adding thermoplastic fibers and partially melt these, the second (WO 97/38654) by adding a chemical binder. Other suitable materials are airlaid composite materials.

Absorbent sandwich webs according to the present invention which are particularly useful as disposable absorbent articles exhibit basis capacities of more than about 8 l/m$^2$, calipers of less than 2 mm and Handle-O-meter values of less than 5 N/200 mm.

An absorbent sandwich web according to the present invention can suitably manufactured by employing techniques as well known for the manufacturing of air-laid structures, such as by using M&J forming heads.

Thus the manufacturing process has a manufacturing direction aligned with the length direction of the absorbent sandwich web and a cross-direction, aligned with the width. Correspondingly, the thickness or z-direction is perpendicular thereto.

The process comprises several steps, which, however do not necessarily be performed in same order as described:

a) The process comprises the step of providing outer layers. Such a layer may be pre-formed and may be provided from roll stock unwinds or out of boxes. Alternatively an outer layer may be formed in the same manufacturing process of forming the sandwich structure, such as by forming a layer of fibers, optionally a mix of fibers. Optionally, such a fibrous batt may be formed on a preformed web. In-line formed layers may undergo a bonding treatment, such as calendering with smooth or embossed, optionally heated rolls.

b) SAM and fibrous material are mixed and laid down, preferably directly onto an outer web, then also referred to as carrier web. Alternatively, the mixture may be laid down first on a laid down aid, such as well known lay down belt or drum, and may then be transferred to a carrier web, or directly sandwiched between a carrier and a cover web. To this end, the cellulosic fibers may be disintegrated by a conventional hammer mill, other fibers, such as synthetic fibers but also SAM in fibrous form may be individualized by other conventional means, such a bale opener or the like. If the SAM is provided in particular form, it can be metered in continuously such as from bulk storage. It is preferred, that both the SAM and the fibrous material are metered in continuously.

The mixing and the lay down can be achieved by conventional air laying apparatuses, such as well known as M&J forming heads, which may require workmanship adaptation towards relatively higher amounts of SAM, in excess of at least 70% of the mix of SAM and fibers. Preferably the lay down is supported by the application of a z-directional vacuum suction. It is highly preferred that the lay down process provides an even and constant distribution of the SAM in particular in the x- and y-direction of the sandwich structure.

Typically, though not necessarily, an outer layer and the SAM and fiber mixture are laid down in a co-terming relationship. Optionally, an outer layer may extend y-directionally outwardly from the SAM and fiber mix.

c) A further outer web, often referred to as a cover web, is positioned over the SAM and fiber mix, thus completing the sandwich structure. Although the cover web may be a pre-formed web, it is a preferred execution that the cover layer is formed in-situ, which may be done in analogy to the defiberization and lay down of fibers in step b). Typically, though not necessarily, an outer layer and the SAM and fiber mixture are laid down in a co-terming relationship. Optionally, an outer layer may extend y-directionally outwardly from the SAM and fiber mix.

d) The process comprises further at least on compaction step. Compaction refers to pressing of the sandwich structure.

d1) A first low pressure compaction may be applied to a carrier web, if this is—at least partly—formed in-situ (or in-line) prior to the addition of the SAM and fiber mix. Low pressure compaction can be performed by using smooth rolls and may ease further processing steps such as by increasing density and integrity, or smoothness of the surface.

d2) A further low pressure compaction may be applied to the SAM and fiber mixed just after lay down.

d3) A moderate pressure compaction can be applied to the sandwich structure by smooth or embossed compaction rolls This moderate pressure compaction aims at compacting the SAM and fiber mixture. A first effect of this moderate compaction is believed to be tamping thereby rearranging primarily particles in a closer and denser relationship. It is further believed, that this moderate pressure compaction creates bonding, such as hydrogen bonding, between the SAM and the other fibers of the mixture, induced by the residual moisture in the materials.

Preferably, the line pressure in the moderate pressure compaction is at more than about 10 N/mm, preferably more than about 15 N/mm Preferably the maximum line pressure applied at any of the compaction steps in calender rolls is less than about 60 N/mm, preferably less than about 30 N/mm, or equivalent, if other compaction tools are applied.

This is considered to be a different mechanism as occurring in mixtures with lower SAM concentrations, such as described in EP1032342 (Maksimov) where bonding is described to occur between cellulosic fibers only.

e) Further, the process comprises steps of applying latex binder to at least one, preferably both of the surfaces of the sandwich structure. The latex binders as described herein above are provided in the form of an aqueous dispersion.

Preferably, they are further diluted so as to provide additional moisture, which may penetrate into the central layer. Equivalently, the dispersions may be applied as supplied and additional moisture may be applied separately.

The process according to the present invention comprises at least two latex binder applications e1) and e2), each one for the outer surfaces of the outer layers. The latex binder may be applied by any conventional application methods with spray application being preferred.

Preferably, a first latex binder application is executed after the complete sandwich structure is formed and has undergone a moderate pressure compaction step (d3). Upon curing of the first applied latex binder, such as by thermal treatment (see below), the absorbent sandwich web may be turned and the second latex may be applied.

If two latex applications are used, these may use the same or different latex binder at same or different dilutions, if employed. In a particular execution, the latex binder dispersion comprises no more than about 40%, preferably less than about 20% of latex binder, based on the weight of binder latex and water in the dispersion. Either during or after application of a latex binder, vacuum may be applied z-directionally to aid penetration of the latex binder into the central layer.

f) The process further comprises at least one thermal treatment step for removing moisture as applied with the latex binder and for curing the latex binder as applied in steps e1) and e2).

The thermal treatment may be any conventional heat treatment, such as application of hot air, or by running the web through ovens or oven sections. Alternative thermal treatments may comprise radiation treatment, such as with infra red or microwave radiation, or any other means for achieving curing of the binder latex.

Optionally, and often preferably, the process comprises more than one thermal treatment steps, e.g. each one directly after each of the applications of the latex binder.

The thermal treatment steps are preferably performed after moderate pressure compaction step d3) is executed, such that the SAM and the fibers in the central layer are in a contacting relationship and further bonding or attachment between the SAM and the fibers is affected.

An additional thermal treatment may be applied to further adjust the moisture content of the web, i.e. to drive off most, preferably all of the water added together with the latex binder.

The thermal treatment is preferably executed at temperatures allowing efficient curing of the latex binder and drying of the web without detrimentally affecting other properties of the web, such as discoloring of cellulose fibers, or melting of synthetic fibers, if present. Hence, it is preferred to operate the thermal treatment at temperatures above 100° C., preferably above 120° C., but preferably below 200° C., more preferably below 180° C., and most preferably at temperatures of about 140° C.

The process may further comprise material finishing steps, such as—without limitation—slitting, winding, spooling, festooning and the like, all well known to a person skilled in the art.

EXAMPLES

After having described both absorbent sandwich webs and processes for the manufacturing of such webs, the following describes exemplarily the making of particular executions and resulting absorbent sandwich webs. A skilled person will readily realize the various possibilities for adjusting process settings to realize material with varying compositions and properties.

Example 1

Referring to FIG. 1, an airlaid manufacturing unit 1000 is schematically depicted, exhibiting a production width for the material of 2.7 m. The manufacturing direction 1010 corresponds to the material length direction.

In an unwind stand 1100 a conventional 17 g/m² paper tissue 1150, available under the designation KB1730-001 from Swedish Tissue AB, Sweden is provided and guided to the forming station 1200, where it is placed on a forming wire (not shown) covering a vacuum suction box 1210. The tissue runs at a machine speed of 31 m/min.

The forming station 1200 comprises three forming heads, 1220, 1230 and 1240 respectively, with the first one 1220 not being used in the present example.

A first cellulosic pulp 1235, here Golden Isles EF-100 Airlaid Fluff pulp Grade 4881, Georgia-Pacific, USA, individualized by a hammer mill (not shown) and a particulate SAM, 1236, here EK-X EN52, of EKOTEC Industrietechnik, Germany, are metered at 90 kg/hr (pulp) and 1600 kg/hr (SAM) into forming head 1230. The materials are homogeneously mixed and evenly deposited both in MD and CD onto the tissue by gravity supported by vacuum of the suction box 1210, resulting in a relatively loose batt 1238 of particulate SAM with pulp fibers interspersed on the tissue.

A second layer of cellulosic fluff, here of the same type as the first and also individualized by a hammer mill (not shown), is metered into a third forming head 1240 at a rate of 90 kg/hr.

A first smooth compaction roller 1310 applies a pressure of 1.5 bar such that the web is slightly densified and the strength is increased to ease further handling.

A web transfer means 1280, such as a further vacuum box, transfers the web to the compacting station 1300, here shown with a patterned roll 1330 acting against a smooth roll 1340, applying 20 N/mm compaction line pressure thereby creating internal bonding and increasing tensile strength.

A first latex binder is applied in the first latex binder application station 1400. To this end, the latex binder, here Vinnapas® 192, commercially available from Wacker Chemie AG, Germany, is diluted from 52% dry matter to about 16% dry matter and sprayed as latex binder dispersion 1410 at a rate of 200 l/hr evenly over the surface of the web. A moderate vacuum is applied by a further vacuum suction box 1420.

The web is guided into a first section 1510 of a drier 1500 operated at a temperature of 140° C., where moisture is dried off.

A further calender station 1350 has not been used in the present example, except for inverting the material such that the tissue surface now faces upwardly.

A second latex binder is applied in the second latex binder application station 1450 to the tissue side of the web. To this end the latex binder, here of the same type as the first latex binder and diluted to form latex binder dispersion 1460, is evenly applied at a rate of 150 l/hr. A moderate vacuum is applied by a further vacuum suction box 1470.

The web is guided into a second section 1520 of a drier 1500 operated at a temperature of 140° C., where moisture is dried off and the latex binder is cured.

The web is guided into a third section 1530 of a drier 1500 operated at a temperature of 140° C., where further moisture may be dried off and the final web moisture content of between about 4% and 6% is reached. The final absorbent sandwich material 1650 can now be guided to a winder 1600 and/or further processed, such as by slitting, block-building or festooning (all not shown).

The resulting web exhibits a composition of
9.4% pulp
83.4% SAM
4.3% tissue
1.6% Latex binder of the first application to the pure pulp surface;
1.3% latex binder of the second application
The resulting web exhibited the following properties
Basis weight: 380 g/m² (EDANA 40.3/WSP130.1);
Thickness (after slitting): 0.95 mm (EDANA 30.5/WSP 120.6);
Tensile MD: 28 N/50 mm (EDANA 20.2/WSP110.4);
Absorption: 41 g/g (EDANA 10.4.02 modified for 10 minutes; 0.9% NaCl);
Absorption: 16 l/m² (EDANA 10.4.02/WSP 10.1 modified for 10 minutes; 0.9% NaCl);
Retention (w-CRC): 26 g/g (EDANA 441.2-02/WSP 241.2; teabag, modified by 10 minutes waiting time and 5 minutes centrifuge time);
Area specific capacity (retention): 10 l/m² (calculated from w-CRC and basis weight)
Stiffness MD: 24 mN*cm (EDANA 50.5/WSP 90.5);
Stiffness to area-specific-capacity ratio: 2.4 (calculated from MD-stiffness and area specific capacity);
Handle-O-meter: MD: 2.8 N/200 mm; CD: 3.0 N/200 mm (EDANA method WSP 90.3.0, modified by evaluating samples of 40 mm×160 mm and by setting the slot width to 20 mm).
Delamination strength: 1.55 N/50 mm (Composite Lamination Strength test, EDANA WSP 401.0 (05))

Example 2

In a second example, the same equipment has been employed and the same material have been used except that the paper tissue has been replaced by a 22 g/m² hydrophilic carded PP nonwoven as supplied by Sandler AG, Germany.

Further the first cellulosic pulp 1235 has been metered in at a rate of 90 kg/hr and the particulate SAM 1236 at a rate of 1500 kg/hr, whilst the addition of the second cellulosic fiber 1245 was retained at 90 kg/hr.

The same latex binder dispersion was applied at rates of 200 l/hr both for the first and the second application.

The resulting web has the following composition:
9.4% pulp;
78.4% SAM;
8.8% carded nonwoven;
1.7% latex binder of the first application to the pure pulp surface;
1.7% latex binder of the second application to the nonwoven web surface;
The resulting web exhibited the following properties
Basis weight: 240 g/m² (EDANA 40.3/WSP130.1);
Thickness (after slitting): 0.95 mm (EDANA 30.5/WSP 120.6);
Tensile MD: 40 N/50 mm (EDANA 20.2/WSP110.4);
Absorption: 44 g/g (EDANA 10.4.02 modified for 10 minutes; 0.9% NaCl);
Absorption: 11 l/m² (EDANA 10.4.02/WSP 10.1 modified for 10 minutes; 0.9% NaCl);
Retention (w-CRC): 25 g/g (EDANA 441.2-02/WSP 241.2; teabag, modified by 10 minutes waiting time and 5 minutes centrifuge time);
Area specific capacity (retention): 6 l/m² (calculated from w-CRC and basis weight)
Stiffness MD: 11 mN*cm (EDANA 50.5/WSP 90.5);
Stiffness to area-specific-capacity ratio: 4.75 (calculated from MD-stiffness and area specific capacity);
Delamination strength: 0.8 N/50 mm (Composite Lamination Strength test, EDANA WSP 401.0 (05))

Comparative Example

On the same line as described in Example 1, a comparative absorbent web has been produced, having an overall content of 30% particulate SAM and 55% pulp, both of the same type as in example 1. Both materials have been homogeneously mixed with 11% of crimped polyethyleneterephthalate (core)/polyethylene (sheath) bicomponent fibers, available under the designation TREVIRA® 255-3.0 dTex, Partie 1653, available from Trevira GmbH, Germany.

Both outer surfaces have been sprayed with each 2% (dry basis) of a vinylacetate-ethylene copolymer latex, DUR-O-SET Elite Ultra-Soft, available from Celanese, The Netherlands.

The material has been compacted and dried to result in a 200 g/m² (EDANA 40.3/WSP130.1) material at a thickness of 1.45 mm (EDANA 30.5/WSP 120.6).

Thus, it represents a typical conventional SAM containing airlaid material, exhibiting a significantly lower capacity at a higher caliper as Example 1.

Nonetheless such a material exhibits a comparable Handle-O-Meter result of 3.0 N/200 mm in MD and 2.4 N/200 mm in CD (EDANA method WSP 90.3.0, modified by evaluating samples of 40 mm×160 mm and by setting the slot width to 20 mm), underlining the superiority of the present invention.

The invention claimed is:

1. Liquid absorbent sandwich web
    said web exhibiting in Cartesian coordinates an (x-directional) length along the machine direction of the manufacturing process, further a thickness or z-direction and a width (y-) direction, and comprising as sandwich forming materials
        a first and a second outer layer, in the form of an in-situ formed or pre-formed web,
        particulate superabsorbent material (SAM), sandwiched between said outer layers;
        individualized fibers adapted to be interspersed between said SAM;
        a self-crosslinking latex binder;
    the sandwich forming materials being present in the following composition:
        SAM from about 70% to about 90%;
        fibers interspersed between the SAM from about 5% to 25%;
        first outer layer from about 2% to about 15%;
        second outer layer from about 2% to about 15%;
        self-crosslinking latex binder from about 1% to about 5%;
        all as weight-% based on the sum of the weights of the sandwich forming materials,
    and wherein said composition is essentially uniform across the x- and y-direction of said web and the SAM particles of the particulate SAM form a particle matrix with the fibers interspersed in interparticle interstices of the particle matrix, and
    wherein the particle matrix with the fibers interspersed in interparticle interstices of the particle matrix is formed by compacting the sandwich forming materials in one or more compaction step(s), wherein the maximum line pressure of any of said one or more compaction steps is less than about 60 N/mm and wherein at least one of said compaction steps is executed at a line pressure of more than about 10 N/mm, such that SAM particles are rearranged in a closer and denser relationship while bonding is created between the SAM particles and the fibers,
    wherein the self-crosslinking latex binder is applied to at least one of the outer surfaces of said outer layers after the liquid absorbent sandwich web is formed and has undergone the one or more compaction step(s), and
    wherein the web exhibits a stiffness to retention capacity ratio as determined by the ratio of the web material stiffness and the area specific capacity, as described herein, of less than 5.0 (mNcm)/(l/m²).

2. A liquid absorbent sandwich web according to claim 1, wherein said self-crosslinking latex is present in at least one of said first and said second outer layer and in the mixture of said SAM and said fibers between said first and said second outer layers.

3. A liquid absorbent sandwich web according to claim 1 further satisfying at least one of the following concentrations:
    SAM from about 80% to about 90%;
    fibers interspersed between the SAM from about 8% to 15%;
    first outer layer from about 2% to about 10%;
    second outer layer from about 2% to about 10%;
    self-crosslinking latex binder from about 2% to about 4%.

4. A liquid absorbent sandwich web according to claim 1, wherein said self-crosslinking latex binder is a vinylacetate-ethylene copolymer.

5. A liquid absorbent sandwich web according to claim 1, further comprising less than about 5% other binder material, based on the amount of SAM, fibers, and binder.

6. A liquid absorbent sandwich web according to claim 1, wherein said web exhibits at least one of the following:
    an absorbent web centrifuge retention capacity which is at least 23 g/g according to a method as described herein;
    an absorbent web centrifuge retention capacity which is at least 85% of the SAM centrifuge retention capacity of the SAM in the web;
    a stiffness to retention capacity ratio as determined by the ratio of the web material stiffness and the area specific capacity, as described herein, of less than 3.0, in units of (mNcm)/(l/m²).

7. A disposable absorbent article
    comprising a topsheet, a backsheet, and a liquid absorbent sandwich web according to claim 1 positioned between said top sheet and backsheet, further comprising an intermediate layer between said liquid absorbent web and said top sheet.

8. A liquid absorbent sandwich web according to claim 1, wherein the first and second outer layers comprise cellulosic fibers.

9. A liquid absorbent sandwich web according to claim 1, wherein the individualized fibers adapted to be interspersed between said SAM comprise cellulosic fibers.

10. A method for making a liquid absorbent sandwich web
    said web exhibiting in Cartesian coordinates an (x-directional) length along the machine direction of the manufacturing process, further a thickness or z-direction and a width (y-) direction;
    said method comprising
        providing as sandwich forming materials
            a first and a second outer layer, in the form of an in-situ formed or pre-formed web;
            particulate superabsorbent material (SAM);
            individualized fibers adapted to be interspersed between said SAM;
            a self-crosslinking latex binder;
        forming a mixture of said SAM and said individualized fibers,
            at a SAM concentration of at least 70% based on the combined weight of SAM and fibers in said mixture;
        forming a sandwich structure of said mixture between said first and said second outer layer at an essentially constant thickness, basis weight and concentration along the (x-)-length and (y-) width direction of said web;
        compacting said sandwich structure in one or more compaction step(s), wherein a maximum line pressure of any of said one or more compaction step(s)

is less than about 60 N/mm and wherein at least one of said compaction step(s) is executed at a line pressure of more than about 10 N/mm such that SAM particles of the particulate SAM are rearranged in a closer and denser relationship while bonding is created between the SAM particles and the fibers, and such that the SAM particles of the particulate SAM form a particle matrix with the fibers interspersed in interparticle interstices of the particle matrix;

applying said self-crosslinking latex binder to at least one of the outer surfaces of said outer layers after the sandwich structure is formed and has undergone the one or more compaction step(s) such that the sandwich forming materials are present in the following composition SAM from about 70% to about 90%;
fibers interspersed between the SAM from about 5% to 25%;
first outer layer from about 2% to about 15%;
second outer layer from about 2% to about 15%;
self-crosslinking latex binder from about 1% to about 5%;
all as weight-% based on the sum of the weights of the sandwich forming materials;

thermally treating said sandwich structure to reduce moisture content and induce crosslinking of said self-crosslinking latex binder, wherein the web exhibits a stiffness to retention capacity ratio as determined by the ratio of the web material stiffness and the area specific capacity, as described herein, of less than 5.0 (mNcm)/(l/m$^2$).

11. A method for making a liquid absorbent sandwich web according to claim 10, wherein the maximum line pressure of any of said one or more compaction steps is less than about 30 N/mm.

12. A method for making a liquid absorbent sandwich web according to claim 10, wherein at least one of said compaction steps is executed at a line pressure of more than 15 N/mm.

13. A method for making a liquid absorbent sandwich web according to claim 10, wherein
said self-crosslinking latex binder is applied as an aqueous solution or dispersion at a self-crosslinking latex binder content of more than 5% and less than about 30%, all based on dry matter of the latex binder in the solution or dispersion.

14. A method for making a liquid absorbent sandwich web according to claim 10, wherein said thermal treatment of said sandwich web is at between 130° C. and 180° C.

15. A method for making a liquid absorbent sandwich web according to claim 10, wherein said thermal treatment is executed until a final overall moisture content of said absorbent web is less than 15%.

16. A method for making a liquid absorbent sandwich web according to claim 10, wherein the first and the second outer layers comprise cellulosic fibers.

17. A method for making a liquid absorbent sandwich web according to claim 10, wherein the individualized fibers adapted to be interspersed between said SAM comprise cellulosic fibers.

18. A method for the making of a liquid absorbent sandwich web according to claim 10, wherein said self-crosslinking latex binder is applied to at least one of the outer surfaces of said outer layers such that the self-crosslinking latex binder is present in the sandwich forming materials at an amount of at least 2% and not more than 4%, based on the dry amount of latex binder in the absorbent web.

19. A method for making a liquid absorbent sandwich web according to claim 10, comprising
applying said self-crosslinking latex binder to said mixture of said SAM and said individualized fibers.

20. A method for making a liquid absorbent sandwich web according to claim 10, comprising
applying vacuum suction z-directionally through said sandwich structure.

* * * * *